US006529543B1

United States Patent
Anderson et al.

(12) United States Patent
(10) Patent No.: US 6,529,543 B1
(45) Date of Patent: Mar. 4, 2003

(54) APPARATUS FOR CONTROLLING LASER PENETRATION DEPTH

(75) Inventors: R. Rox Anderson, Lexington, MA (US); Yacov Domankevitz, Brookline, MA (US)

(73) Assignee: The General Hospital Corporation, Boston, MA (US)

( * ) Notice: Subject to any disclaimer, the term of this patent is extended or adjusted under 35 U.S.C. 154(b) by 81 days.

(21) Appl. No.: 09/717,779

(22) Filed: Nov. 21, 2000

(51) Int. Cl.[7] .............................. H01S 3/08; A61B 18/18
(52) U.S. Cl. ........................ 372/108; 606/13; 606/16; 606/17
(58) Field of Search ........................ 372/108; 606/13, 606/16, 17

(56) References Cited

U.S. PATENT DOCUMENTS

| | | |
|---|---|---|
| 4,122,342 A | 10/1978 | Vali et al. |
| 4,273,127 A | 6/1981 | Auth et al. |
| 4,387,954 A | 6/1983 | Beasley |
| 4,400,056 A | 8/1983 | Cielo |
| 4,447,546 A | 5/1984 | Hirschfeld |
| 4,585,298 A | 4/1986 | Mori |
| 4,660,925 A | 4/1987 | McCaughan, Jr. |
| 4,672,961 A | 6/1987 | Davies |
| 4,707,201 A | 11/1987 | Failes |
| 4,712,543 A | 12/1987 | Baron |
| 4,799,479 A | 1/1989 | Spears |
| 4,852,567 A | 8/1989 | Sinofsky |
| 5,042,980 A | 8/1991 | Baker et al. |
| 5,122,060 A | 6/1992 | Vassiliadis et al. |
| 5,207,669 A | 5/1993 | Baker et al. |
| 5,248,311 A | 9/1993 | Black et al. |
| 5,254,114 A | 10/1993 | Reed, Jr. et al. |
| 5,342,352 A | 8/1994 | Franken et al. |
| 6,126,655 A | * 10/2000 | Domankevitz et al. ....... 606/17 |
| 6,129,723 A | * 10/2000 | Anderson et al. ............. 606/13 |
| 6,350,261 B1 | * 2/2002 | Domankevitz et al. ....... 606/17 |

FOREIGN PATENT DOCUMENTS

| | | |
|---|---|---|
| EP | 0400802 A2 | 12/1990 |
| GB | 2154761 A | 9/1985 |
| GB | 2222881 A | 3/1990 |
| WO | 9102562 | 3/1991 |
| WO | WO95/17924 | 7/1995 |

OTHER PUBLICATIONS

Cox et al., "New method for exposing mammalian cells to intense laser radiation using the evanescent fields created in optical waveguides," *Med. Phys.* 5:274–279 (1978).

* cited by examiner

*Primary Examiner*—Paul Ip
*Assistant Examiner*—James Menefee
(74) *Attorney, Agent, or Firm*—Fish & Richardson P.C.

(57) ABSTRACT

The invention features systems and tools for controlling the optical penetration depth of laser energy, e.g., when delivering laser energy to target tissue in a patient. The systems and tools control the optical penetration depth (OPD) by controlling the incident angle at which the laser energy is delivered to the target area of the patient. Embodiments of the invention include an optical coupler that permit a user to vary the incident angle and thereby selectably control the OPD of incident laser energy. Fabricating the optical coupler to have a refractive index greater than that of the target tissue can enhance the range of selectable OPDs. The laser energy, which is delivered to the desired depth, can cause alteration of the target tissue by, e.g., heating, ablation, and/or photochemical reaction.

36 Claims, 6 Drawing Sheets

APPARATUS FOR CONTROLLING LASER PENETRATION DEPTH

FIELD OF THE INVENTION

This invention relates to the use of electromagnetic wave energy to alter a substrate, e.g., by heat, ablation, and/or photochemical reaction.

BACKGROUND OF THE INVENTION

Lasers are useful in medical, materials processing, and other applications to cause heating and/or ablation, i.e., substance removal, within a substrate, e.g., biological tissue or other material. In addition, certain lasers, e.g., ultraviolet (UV) lasers, can be used to cause photochemical alterations, e.g., polymerization, in a substrate, with or without simultaneous ablation.

Laser energy is typically delivered as a beam or illumination in which the electromagnetic energy propagates directly into the tissue or other substrate. Ablation of biological tissue by lasers occurs predominantly by the rapid thermal vaporization of tissue water. However, secondary processes may coexist with this thermal vaporization. For example, explosive mechanical removal is caused by short laser pulses when laser energy intensity is high enough to initiate a plasma that produces shock waves and mechanical fracture, e.g., greater than about $10^8$ W/cm$^2$. Additionally, UV pulsed laser ablation can cause concurrent photochemical reactions in tissue. When present, these secondary processes can change the efficiency of pulsed laser ablation.

The ablation depth within tissue or other materials depends upon the depth to which the electromagnetic waves penetrate. For some applications, e.g., treatment of large tumors, deep or subsurface penetration is required, and appropriate wavelength regions, e.g., red or near infrared, are preferable. For other applications, a well-controlled superficial effect is desired, e.g., skin resurfacing, ablation of the outer surface of the cornea to correct vision, or of the inner surface of diseased arteries. Typically, laser energy is delivered to a patient at normal incidence, and the wavelength of the laser energy is selected to produce the desired penetration depth based on the optical absorption of the target tissue and any intermediate tissue.

SUMMARY OF THE INVENTION

The invention features systems and tools for controlling the optical penetration depth of laser energy, e.g., when delivering laser energy to target tissue in a patient. The systems and tools control the optical penetration depth (OPD) by controlling the incident angle at which the laser energy is delivered to the target area of the patient. Embodiments of the invention include an optical coupler that permit a user to vary the incident angle and thereby selectably control the OPD of incident laser energy. Fabricating the optical coupler to have a refractive index greater than that of the target tissue can enhance the range of selectable OPDs. The laser energy, which is delivered to the desired depth, can cause alteration of the target tissue by, e.g., heating, ablation, and/or photochemical reaction.

In general, in one aspect, the invention features an apparatus delivering laser radiation to a substrate at a controlled penetration depth, the substrate having a first refractive index and an absorption coefficient $\mu_a$. The apparatus includes an optical coupler for receiving optical energy from a optical energy source and a positioning mechanism. The optical coupler has a second refractive index higher than the first refractive index and is adapted to contact and form an interface with the substrate. It also has a contoured surface such that an angle of refraction $\theta_r$ of the optical energy into the substrate at the interface can be varied by adjusting relative positions of the optical coupler and the optical energy entering the optical coupler. Selection of a particular angle of refraction produces a desired penetration depth $\delta_r$ according to the equation $\delta_3 \approx (1/\mu_a)\cos\theta_r$. The positioning mechanism couples the optical coupler and the optical energy to adjust the relative positions of the optical coupler and the optical energy entering the optical coupler.

The optical coupler may have, e.g., a hemispherical shape or a hemicylindrical shape. The positioning mechanism can be angular positioning mechanism, for example, it can include a gimbal mounted to the optical coupler. Alternatively, the positioning mechanism can be a translational positioning mechanism, e.g., it can include a support structure slidably connected to the optical coupler. Furthermore, the optical coupler can be configured to receive the optical energy at substantially normal incidence and deliver the optical energy to the interface at non-normal incidence.

In general, in another aspect, the invention features, another apparatus delivering laser radiation to a substrate at a controlled penetration depth, the substrate having a first refractive index $n_1$ and an absorption coefficient $\mu_a$. The second apparatus includes an optical coupler for receiving optical energy from a optical energy source. The optical coupler has a second refractive index $n_2$ higher than the first refractive index. The optical coupler also has at least two surfaces adapted to contact and form an interface with the substrate. It is shaped to internally direct the optical energy received from the optical energy source to the first surface at a first acute incident angle, and direct optical energy internally reflected from the first surface to the second surface at a second acute incident angle different from the first acute incident angle. Contacting the substrate with the first surface produces an optical penetration depth $\delta_{r1} \approx (1/\mu_a)\cos\theta_{r1}$, whereas contacting the substrate with the second surface produces an optical penetration depth $\delta_{r2} \approx (1/\mu_a)\cos\theta_{r2}$, where $\theta_{r1}$ is the refraction angle corresponding to the first acute incident angle and $\theta_{r2}$ is the refraction angle corresponding to the second acute incident angle.

The optical coupler may further include a third surface adapted to contact and form an interface with the substrate. In this case, the optical coupler is shaped to direct the optical energy internally reflected from the second surface to the third surface at a third acute incident angle. In some embodiments, the first and second acute incident angles can both greater than $\arcsin(n_0/n_2)$, $n_0$ being the refractive index for air, and/or they can both be less than $\arcsin(n_1/n_2)$. Furthermore, the first and second acute incident angles can be each greater than about 10°.

In general, in another aspect, the invention features another apparatus delivering laser radiation to a substrate at a controlled penetration depth, the substrate having a first refractive index $n_1$ and an absorption coefficient $\mu_a$. The third apparatus includes: an optical coupler base; and a plurality of optical coupler tips each configured to be mechanically attached to the optical coupler base to form an optical coupler for delivering optical energy from a optical energy source to a substrate. The optical coupler includes a surface adapted to contact and form an interface with the substrate. Each optical coupler tip, when attached to the optical coupler base, is shaped to internally deliver the optical energy to the interface at an incident angle, wherein the incident angles corresponding to each of the plurality of optical coupler tips differ from one another. Selecting one of the optical coupler tips specifies a desired penetration depth $\delta_r$, according to the equation $\delta_r \approx (1/\mu_a)\cos\theta_r$, where $\theta_r$ is the refraction angle corresponding to the incident angle defined by the selected optical coupler tip.

In some embodiments, each of the optical coupler tips has a refractive index greater than the first refractive index $n_1$. Moreover, the plurality of optical coupler tips may include at least three optical coupler tips. The incident angle defined by each optical coupler tip may be greater than about 10°. Furthermore, the incident angle defined by each optical coupler tip may be greater than $\arcsin(n_0/n_2)$, where $n_0$ is the refractive index for air and $n_2$ is the refractive index of the respective optical coupler tip. Also, the incident angle defined by each optical coupler tip may be less than $\arcsin(n_1/n_2)$, where $n_2$ is the refractive index of the respective optical coupler tip.

Embodiments of any of the first, second, and third apparatus described above may include any of the following features.

The apparatus may include an optical fiber mechanically coupled to the optical coupler or optical coupler base. The optical coupler or each of optical coupler tips may be made from one of sapphire, fused silica, BK-7 glass, flint glass, germanium, and zinc selenide. The apparatus may further including the optical energy source. The optical energy source may includes a Nd:YAG laser, CTE:YAG laser, ErCr:YSGG laser, holmium laser, erbium laser, $CO_2$ laser, diode laser, or dye laser. For example, suitable wavelength ranges include 1.7 to 2.2 $\mu$m, 2.7 to 3.2 $\mu$m, 10.6 $\mu$m, and 420 to 510 nm.

In general, in another aspect, the invention features a method of removing wrinkles in a region of skin. The method includes: applying an optical coupler to the region to cause a surface of the optical coupler to contact the ridges of the wrinkles and be spaced from the valleys of the wrinkles; and delivering optical energy from a optical energy source through the optical coupler to the surface at an incident angle that is greater than about $\arcsin(n_0/n_2)$ and less than about $\arcsin(n_1/n_2)$, where $n_0$, $n_1$, and $n_2$ are the refractive indices of air, the skin, and the optical coupler, respectively. The optical energy is delivered with energy sufficient to smooth over the ridges of the wrinkles.

Embodiments of the method may include any of the following features.

The optical energy may be delivered to the optical coupler though an optical fiber. The optical coupler may be made from one of sapphire, fused silica, BK-7 glass, flint glass, germanium, and zinc selenide. The optical energy source may include a Nd:YAG laser, CTE:YAG laser, ErCr:YSGG laser, holmium laser, erbium laser, $CO_2$ laser, diode laser, or dye laser. For example, suitable wavelength ranges include 1.7 to 2.2 $\mu$m, 2.7 to 3.2 $\mu$m, 10.6 $\mu$m, and 420 to 510 nm.

In addition to animal and human tissue, the substrate treated by these methods or apparatus may also be a plastic, polymer, gel, a photosensitive coating, or other material that can be ablated and/or heated by optical energy. To provide laser-induced photochemical alteration of a substrate, UV optical energy may be used, e.g., from an excimer laser.

Unless defined otherwise, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications and patents mentioned herein are incorporated by reference. In addition, the materials, methods, and examples are illustrative only and not intended to be limiting.

The embodiments of the invention include several advantages.

For example, the optical couplers permit a user to selectively control the optical penetration depth of laser energy delivered to a target. Moreover, the material and geometry of the coupler can prevent laser energy from exiting it when it is not contacting the target. The control over OPD permits precise photomedical alteration of tissue. Applications of the new device include superficial alteration of skin, wrinkle removal, corneal ablation laser angioplasty and other endoluminal ablation, dental applications, and laser lithotripsy.

Other features and advantages of the invention will be apparent from the following description of the preferred embodiments thereof, and from the claims.

DETAILED DESCRIPTION

Figure 1:
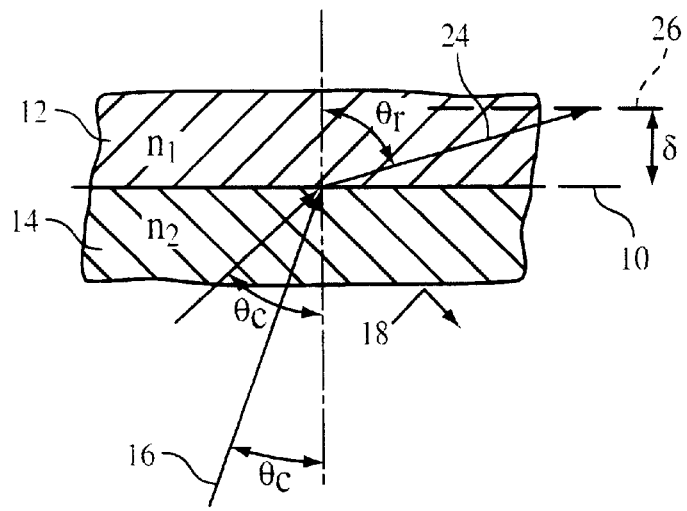
FIG. 1 is a diagrammatic representation of the physics of refracted waves at an interface between two media of different refractive indices.

The present invention features laser energy optical couplers that control the incident angle of laser energy being delivered to a target. The control of the incident angle permits a user to select and vary the optical penetration depth of the laser energy.

Normal Incident Treatment

In general, thermally-driven processing (e.g., ablation or photochemical alteration) of a substrate, e.g., biological tissue, in air by normally-incident, well-absorbed short laser pulses may be described by a first-order model which reveals relationships between tissue optical absorption, depth of ablation and thermal injury, and the laser pulse duration and fluence (energy/area) needed for ablation. The normally-incident laser energy is absorbed by the substrate according to Beer's law, i.e., the intensity I(z) inside the substrate decreases exponentially with depth z:

$$I(z) \approx I_o e^{-\mu_a z}, \quad (1)$$

where $\mu_a$ is the optical absorption coefficient of the substrate, and $I_o$ is the incident irradiance. With the laser energy delivered at normal incidence, the characteristic optical penetration depth, $\delta$, is given by:

$$\delta = 1/\mu_a, \quad (2)$$

which is the thickness of the layer in which most of the laser energy is absorbed. In this layer, the incoming energy is converted to heat, which immediately begins to diffuse to the surroundings. The most precise, efficient ablation is achieved when the thermal energy is confined to this layer, i.e., when the laser energy is delivered before the time needed for significant cooling of the layer. This concept defines a "short" laser pulse, which is suitable for use in the present invention. A short laser pulse has a pulsewidth, $\tau_p$, less than the thermal relaxation time, $\tau_r$, of the layer in which energy is absorbed ($\tau_p < \tau_r$). The thermal relaxation time, $\tau_r$, is related to heat conduction by:

$$\tau_r \approx \delta^2/\alpha \tag{3}$$

where $\alpha$ is the thermal diffusivity of the tissue (e.g., for endoluminal tissue this value is $1.3 \times 10^{-3}$ cm$^2$/sec). For a normally-incident beam, therefore:

$$\tau_r \approx (\mu_a^2 \alpha)^{-1} \tag{4}$$

The incident fluence, $F_o$ (energy/area), necessary for tissue ablation is given by the requirement that the heat of vaporization for tissue water be delivered at the tissue/device interface by each pulse. The energy absorbed per unit volume, $E_v$, at the interface is given by:

$$E_v = F_o \mu_a \tag{5}$$

Experimental data with a variety of pulsed lasers suggests that tissue ablation requires $E_v \sim 2500$ J/cm$^3$ (similar to vaporization of pure water) such that ablation is reliably achieved when $F_o \sim 2500/\mu_a$.

With each short laser pulse of sufficient incident energy, a layer of approximately $\delta$ in thickness is removed, and a layer equal to or greater than $\delta$ remains as thermally-denatured tissue. The thickness of this remaining thermally-denatured tissue is important during wound healing.

This model reveals the primary importance of $\delta$, the optical penetration depth, not only for determining the scale of the tissue layer removed and residual thermal damage, but also for choosing the optimal laser wavelength and pulsewidth. For the least thermal damage and best efficiency of ablation, $\tau_p < \tau_r$, and hence in practice the optimal laser pulsewidth $\tau_p$ varies with $\tau_r$. For $\delta \sim 1$ $\mu$m and $\alpha = 1.3 \times 10^{-3}$ cm$^2$/sec, $\tau_r$ is as low as about 1 $\mu$s.

If tissue ablation is to be carried out with $\mu$m scale precision using normally-incident laser pulses, a wavelength must be chosen for which the tissue absorption is high enough, i.e., $\mu_a \sim 10^4$ cm$^{-1}$, such that $\delta = 1/\mu_a$ $10^{-4}$ cm $= 1$ $\mu$m. Such high tissue absorption coefficients are difficult to achieve, and occur only in the far ultraviolet below 220 nm and at the strongest infrared water absorption band at 2.94 $\mu$m. Ideally, even greater precision could be obtained if $\delta$ were significantly less than 1 $\mu$m.

Radiation Delivered From A Solid Interface at Non-Normal Incidence

Refraction and reflection at a planar boundary between two media, each having a different refractive index, is classically described by Snell's law and Fresnel's equations. Referring to FIG. 1, for refraction from a medium 14 of higher refractive index $n_2$, to a medium 12 of lower refractive index $n_1$, Snell's law states that:

$$n_2 \sin \theta_i = n_1 \sin \theta_r \tag{6}$$

where $\theta_i$ is the angle of incidence and $\theta_r$ is the angle of refraction. "Total" internal reflection 18 occurs at the interface 10 when the angle of incidence is greater than or equal to a critical angle $\theta_c$ given by $\theta_c = \arcsin n_1/n_2$. This reflection is referred to as "total," because when medium 12 absorbs light at the wavelength of the incident radiation, a certain amount of energy is still present in the external medium in a thin layer just past the interface 10.

In particular, when medium 12 absorbs light at the wavelength of incident beam 16, as is typically the case when medium 12 corresponds to tissue, the interaction is more accurately described using the following real-valued set of simultaneous equations:

$$n_2 \sin \theta_i = n' \sin \theta_r, \tag{7a}$$

$$(n_1)^2 - (k_1)^2 = (n')^2 - (k')^2, \tag{7b}$$

$$(n_1)(k_1) = (n')(k') \cos \theta_r, \tag{7c}$$

where $n_1$ and $k_1$ are the refractive index and extinction coefficient of medium 12, respectively, at normal incidence, where n' and k' are the refractive index and extinction coefficient of medium 12, respectively, at the arbitrary incident angle $\theta_i$, and where $k_1$ is related to the absorption coefficient $\mu_a$ according to $k_1 = (\lambda \mu_a)/(4\pi)$, $\lambda$ being the wavelength of the radiation.

Simultaneously solving Equations 7a, 7b, and 7c, provides the exact value for the angle of refraction $\theta_r$ in the presence of absorption. Because the refracted beam 24 propagates into medium 12 at an angle, the refracted beam optical penetration depth $\delta_r$ is reduced, compared with normally-incident radiation. For example, for weak absorption, the optical penetration depth $\delta_r$ can be expressed as:

$$\delta_r = (1/\mu_a) \cos \theta_r \tag{8},$$

in which case the penetration depth is reduced by a factor of $\cos \theta_r$, compared with normally-incident radiation. In practice, this can reduce the penetration depth by up to about one order of magnitude. Moreover, the penetration depth can be controlled by varying the incident angle $\theta_i$ to cause a corresponding change in the refracted angle $\theta_r$ according to Equations 7a, 7b, and 7c.

Table 1 below shows predicted penetration depth $\delta_r$ for refracted beams from an interface for 2.1 $\mu$m wavelength holmium laser radiation ($\mu_a \approx 25$ cm$^{-1}$ in most tissues). Also shown are the thermal relaxation time, $\tau_r$, assuming a thermal diffusivity for tissue, $\alpha$, of $1.3 \times 10^{-3}$ cm$^2$/sec, and the approximate minimum depth of residual thermal injury ($\approx 2\delta_r$).

TABLE 1

| Angle of Refraction ($\theta_r$, degrees) | Optical Penetration Depth ($\delta_r$, $\mu$) | Thermal Relaxation Time ($\tau_r$, seconds) | Min. Thermal Injury Depth ($\mu$m) |
|---|---|---|---|
| 0 (normal) | 200 | 0.3 | 400 |
| 45 | 140 | 0.15 | 280 |
| 80 | 50 | 0.15 | 280 |
| 85 | 20 | 0.003 | 40 |

It is apparent from Table 1 that a refracted wave generator for holmium laser radiation operating at $\theta_r = 85°$ would reduce the penetration depth, and hence the thermal injury and deposited energy per unit area, by an order of magnitude compared to a normally incident laser beam. Standard, normal-mode holmium lasers in surgical use operate at pulse durations of 100 to 300 $\mu$s, such that $\tau_p < \tau_r$ even for a refracted beam at $\theta_r = 85°$. Thus, a device that produces near-surface refraction can be pumped by existing, normal-mode holmium lasers.

The energy needed for superficial alteration such as ablation by these refracted waves is calculated as follows. At a refractive interface, the incident fluence is given by:

$$F_o = (1-R) F_b \cos \theta_i / \cos \theta_r, \qquad (9)$$

where R is the Fresnel reflectance from the interface, and $F_b$ is the fluence of the beam from the laser propagating into medium 14. R depends on the indices of the two media, the angle of incidence and the polarization according to Fresnel's equations. As noted above, reliable short-pulse ablation is achieved when $E_v \approx 2500 (\text{J/cm}^3)$. R is typically 0.8 to 0.9 for such near-surface refraction, depending on $n_1$. Combining equations and solving for $F_b$ (for ablation), the beam fluence in medium 14, gives:

$$F_{b(ablation)} \approx 2500 \cos \theta_r / [\mu_a (1-R) \cos \theta_i] \qquad (10)$$

Absent significant absorption, refracted beam 24 is produced whenever the angle of incidence $\theta_i$ is less than the critical angle for total internal reflection $\theta_c$. This physical constant is used to construct a refracted wave generator such that it radiates refracted waves into the target substrate to be ablated when the generator interface 10 is contacting the substrate. However, the wave generator is also constructed so that no refracted waves are generated when laser energy 16 is delivered across interface 10 to a medium, e.g., air or water, other than the target substrate. This is achieved by selecting an incidence angle, $\theta_i$, greater than or equal to the critical angle, $\theta_c$, for total internal reflection when the generator is not contacting the target substrate, i.e., when it is air, water, or bodily fluids, depending on the desired use of the device.

For example, the critical angle, $\theta_c$, for a germanium (Ge)/air interface is 14°, and for a Ge/tissue interface is 20°. A Ge rod with the distal end ground and polished at 16° from perpendicular to the central axis will provide an incidence angle, $\theta_i$, of 16°. With this incidence angle, laser energy would be coupled into the tissue as refracted waves because the incidence angle is less than the critical angle for total internal reflection for the Ge/tissue interface, but laser energy would not radiate into air because the incidence angle is greater than the critical angle for total internal reflection for the Ge/air interface.

This is an important safety feature and useful advantage of the invention over present surgical laser delivery devices. No beam is allowed to propagate away from the device when it is not contacting the desired substrate, hence it is unlikely to accidentally ignite materials such as surgical drapes, clothing, etc., or to damage substrate, e.g., healthy tissue, adjacent the target area. Because energy is coupled directly into the substrate, e.g., tissue, only on contact, it is also easier to perform precise surgical ablation.

The present invention also provides another safety benefit that results from a phenomenon that occurs with the ablation of tissues according to the invention, which is essentially absent with normally incident beam delivery. During short laser pulse ablation, vapor cavitation and mechanical injury occur in part because the ablation produces thermal confinement, and causes a sudden increase in temperature and pressure at the site of energy absorption, with superheating of tissue water during the laser pulse. Thermal expansion occurs, the pressure decreases, and vaporization begins. The onset of vaporization typically requires 0.5 to 2 $\mu$s even for high-energy submicrosecond pulses, and vaporization continues long after the pulse has been delivered. When the external medium is air, the vapor expands freely from the tissue surface. However, when the external medium is a fluid or tissue, a rapidly-expanding vapor cavity is formed, which grows and then violently collapses on a micro- to millisecond time scale.

In contrast to free-beam ablation, during which laser energy continues to be delivered during the vaporization and ablation process, as soon as vaporization begins with any superficial refracted wave generator, the tissue is transiently replaced by a growing vapor cavity. Total internal reflection will then occur at the device/tissue interface until the vapor cavity collapses. Thus, the vaporization process at a refractive interface temporarily "turns off" its own energy source, by decoupling transmission through the interface.

This self-limiting feature also occurs in devices for superficially altering substrates located in fluids, where the device is designed not to propagate a refracted wave into the fluid, or air, when not in contact with the substrate.

Refracted waves can be generated in tissue and other substrates using standard optical materials for medium 14. Sapphire is, e.g., a desirable material for making a practical wave generator because of its high refractive index, broad optical transmittance band, and extreme thermal and mechanical ruggedness. For a sapphire device (n=1.7), to achieve an angle of refraction, $\theta_r$, of 85°, the angle of incidence, $\theta_i$, must be 50°. Setting R=0.9 and $\mu_a \approx 50$ cm$^{-1}$ (tissue absorption coefficient value when using a holmium laser), the beam fluence required for ablation, $F_b$, will be about 67 J/cm$^2$, which is only slightly higher than the ablative fluence of 50 J/cm$^2$ required for free-beam ablation. Thus, a practical refracted wave generator is relatively efficient.

This may seem paradoxical because R is 0.9, i.e., 90% of the energy incident on the interface is reflected rather than being absorbed. However, as shown in Table 1 above, the energy transmitted through the interface is deposited in a much thinner layer. The order of magnitude "lost" by reflectance is "regained" by the order-of-magnitude decrease in the layer thickness, and hence volume, into which the energy is deposited.

To demonstrate the relationship between incident angle and optical penetration depth, laser energy from a Ho:YAG laser was coupled to porcine skin through hemi-cylindrical sapphire prism. The shaved full-thickness porcine skin with subcutaneous fat was obtained immediately post-mortem and placed in contact with the prism and irradiated at multiple sites corresponding to different angles of incidence. The tissue was then fixed in 10% formalin, embedded in paraffin, sectioned and stained with hematoxylin and eosin. Histological sections corresponding to incident angles of 0°, 30°, and 40° showed a residual zone of thermal damage through a depth of 650 microns, 250 microns, and 100 microns, respectively.

Optical Coupler Devices

Figure 2:
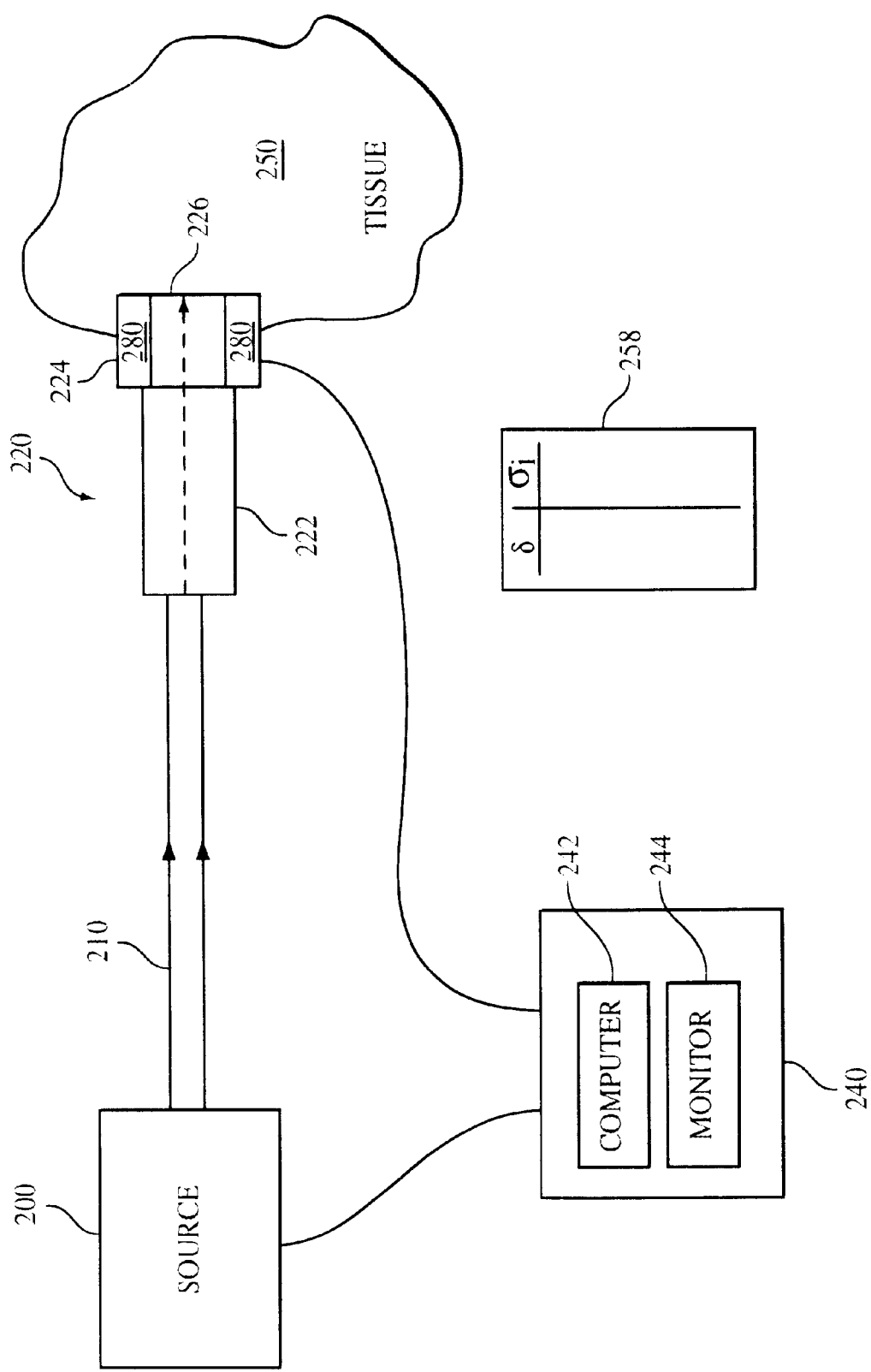
FIG. 2 is a schematic diagram of a system for coupling laser energy into a patient's tissue.

A system delivering laser energy to a patient is shown schematically in FIG. 2. A source 200, e.g., a laser and associated electronics and/or modulators, provides the laser energy to an optical fiber 210, which delivers the laser energy to an optical coupler 220. In the presently described embodiment, the optical coupler device 220 includes a handheld component 222 and a tissue-contacting component 224. A surgeon manipulates and positions optical coupler device 220 relative to tissue 250 using hand-held component 222. The tissue-contacting component 224 includes at least one tissue-contacting surface 226, which forms an interface with tissue 250. The optical coupler device 220 and tissue-contacting surface(s) are designed to permit the surgeon to deliver laser energy to the tissue at one of multiple, selectable incident angles, thereby controlling the optical penetration depth of the laser energy into the tissue. The optical coupler device may further include a cooling element 280 adjacent the tissue-contacting surfaces to cool the tissue nearest the surface, and thereby localize the heating caused by the laser energy at some intermediate depth.

The optical coupler device 220 may further include one or more optical fibers (not shown) adjacent the tissue-contacting surface for visualizing the tissue prior to, and during, the delivering of laser energy. Such visualization fibers are coupled to detectors in an electronic processing system 240, which can further include a computer 242 and a display monitor 244. Alternatively, the visualization fibers can be replaced by a CCD camera coupled to electronic processing system 240 and positioned adjacent the tissue-contacting surface. Cooling elements 280 are also coupled to electronic processing system 240, which controls the temperature of the cooling elements.

The optical coupler device 220 can also be connected to the electronic processing system 240 to provide automated control over the selected incident angle for delivering the laser energy into tissue 250 at a desired penetration depth. Alternatively, when the incident angle is selected by manual manipulation of optical coupler device 220, the electronic processing system 240 can provide information correlating a desired penetration depth with the manipulation of the optical coupler device. In either case, information regarding the laser energy wavelength, the refractive index of the coupler, the refractive index and extinction coefficient of the tissue, and desired penetration depth can be inputted and/or previously stored in the electronic processing system, which then determines the incident angle $\theta_i$ corresponding to the desired penetration depth $\delta_r$ according to Equations 7a, 7b, 7c, and 8. The electronic processing system 240 may further correlate the incident angle $\theta_i$ with a corresponding manipulation of the optical coupler device 220, which may be done manually by the surgeon or in automated fashion by the electronic processing system 240 through transducers (not shown) in the optical coupler device 220.

In embodiments where the manipulation of the optical coupler device is performed manually, information correlating the optical coupler orientation to a desired penetration depth can also be printed on the optical coupler device or on a separate chart 258, for one or more types of tissue and/or laser energy wavelengths.

The source 200 can also be coupled to the electronic processing system 240 to synchronize control the delivery of the laser energy to the optical coupler device 220.

In other embodiments, the optical coupler device may be part of a catheter system for use in endoluminal photoablation applications. In such cases, the optical coupler device can be manipulated using guidewires and other techniques common to the catheter applications.

Figure 3A:
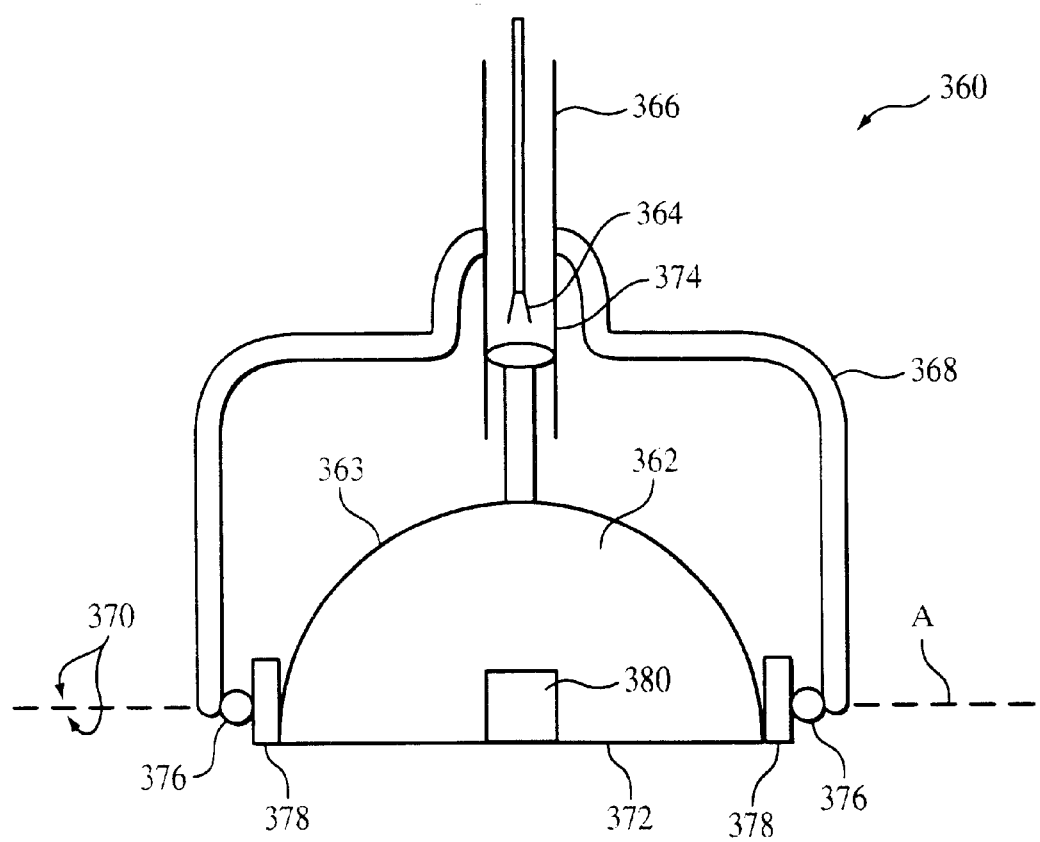
FIGS. 3a and 3b are schematic diagrams of an optical coupler device.

A particular design for an optical coupler is shown in FIG. 3a. Optical coupler device 360 includes an optical coupler 362 with a skin contacting surface 372 and a contoured surface 363. Laser energy 364 is delivered to optical coupler 362 through a delivery conduit 366. Delivery conduit 366 is rotatably mounted to optical coupler 362 by a gimbal 368 for rotation relative to optical coupler 362 about an axis, A, (arrow 370).

In the presently described embodiment, optical coupler 362 is shaped, e.g., hemispherical or hemicylindrical, such that laser energy 364 impinges contoured surface 363 at a 90 degree angle regardless of the angular position of gimbal 368 relative to contoured surface 363, thereby optimizing transmission into optical coupler 362. Thus, the angular position of gimbal 368 set by the user controls the angle of incidence of laser energy 364 impinging skin contacting surface 372 of optical coupler 362. As discussed above, this controls the angle of refraction of laser energy 364 into the tissue, and thus the depth of penetration of the laser energy into the tissue.

Laser energy 364 is collimated by a lens 374 prior to entering optical coupler 362. Laser energy 364 is delivered to lens 374 by, e.g., an optical fiber 376. Alternatively, laser energy 364 can be delivered to lens 374 as a free beam. Gimbal 368 is mounted to optical coupler 362 by, e.g., two ball and socket joints 376 having a desired degree of friction to maintain gimbal 368 at a user selected angular position. Alternatively, the optical coupler device 360 can include a locking mechanism (not shown) for fixing the relative position of gimbal 368 and optical coupler 362.

The route of optical coupler 362 across the skin surface can be tracked by mounting at least one encoder wheel 378 (two encoder wheels being shown in FIG. 3a) to optical coupler 362. The encoder wheel(s) rotate as optical coupler 362 is moved across the skin surface. As encoder wheel 378 rotates, the distance optical coupler moves is monitored. The signal from encoder wheel 378 can be fed to the electronic processing system described above to control the delivery of laser energy into the tissue and to, e.g., prevent multiple treatments of the same tissue area.

When the target tissue is subsurface tissue, optical coupler 362 can also be used to cool the surface tissue before irradiation, during irradiation, and after irradiation, to protect the surface tissue from thermal damage. To this end, a thermocouple element 380 is mounted to optical coupler 362. Preferably two thermocouple elements are mounted to the surface of optical coupler 362 180 degrees apart.

Figure 3B:
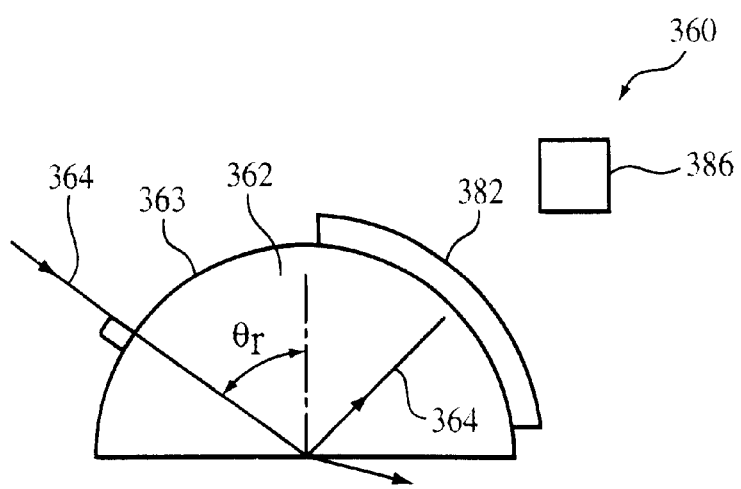

For safety reasons, it is advantageous to prevent free beam propagation of laser energy from optical coupler 362 into the surrounding environment. Referring to FIG. 3b, which is a side view of device 360 shown with gimbal 368 removed, a reflecting film 382, which directs reflected laser energy 384 back into optical coupler 362, is located on the surface 363 of optical coupler 362. The reflecting film 382 redirects the laser energy back to the optical coupler/tissue interface at the same incident angle. Alternatively, a beam dump 386, e.g., a black body with a cooler, located spaced from optical coupler 362 and in the path of beam 384 can be used to absorb the laser energy. In addition, a detector can be positioned at the beam dump to measure the reflectance and guide the incident angle position in either a manual or automated procedure.

As described above, optical coupler device 360 can also include one or more transducer elements (not shown) for providing electronic control of the relative position of the gimbal 368 and optical coupler 362. Furthermore, as described above, information correlating the gimbal orientation to a desired penetration depth can also be printed on the optical coupler device or on a separate chart (not shown), for one or more types of tissue and/or laser energy wavelengths.

The embodiment shown in FIGS. 3a and 3b provide one example of how an optical coupler device can include multiple components (the gimbal and optical coupler) that can be adjustably oriented relative to one another to vary the angle of incidence of laser energy on a tissue-contacting surface. Another example is shown in FIGS. 4a and 4b.

Figure 4A:
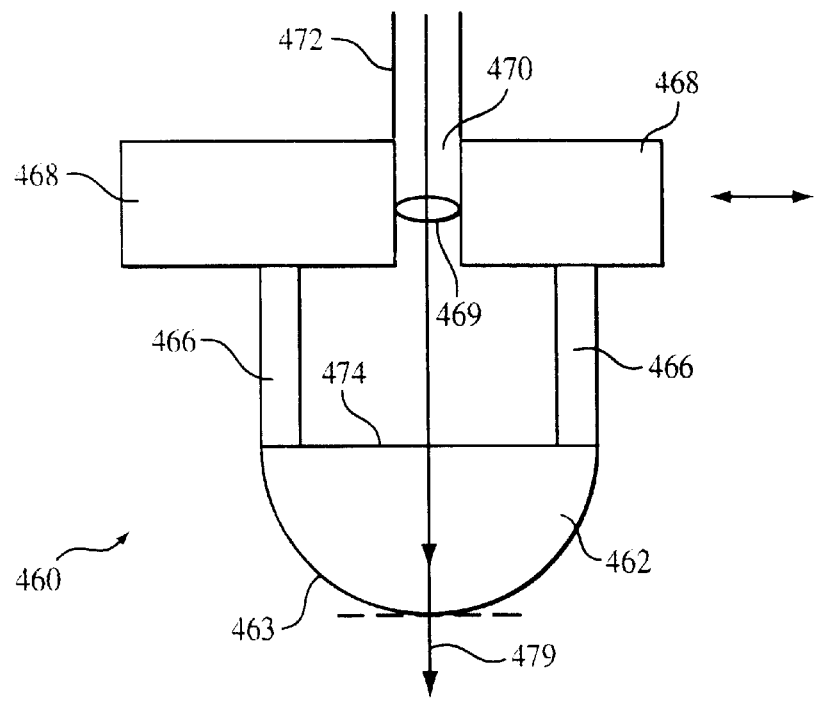
FIGS. 4a and 4b are schematic diagrams of another embodiment of an optical coupler device.
Figure 4B:
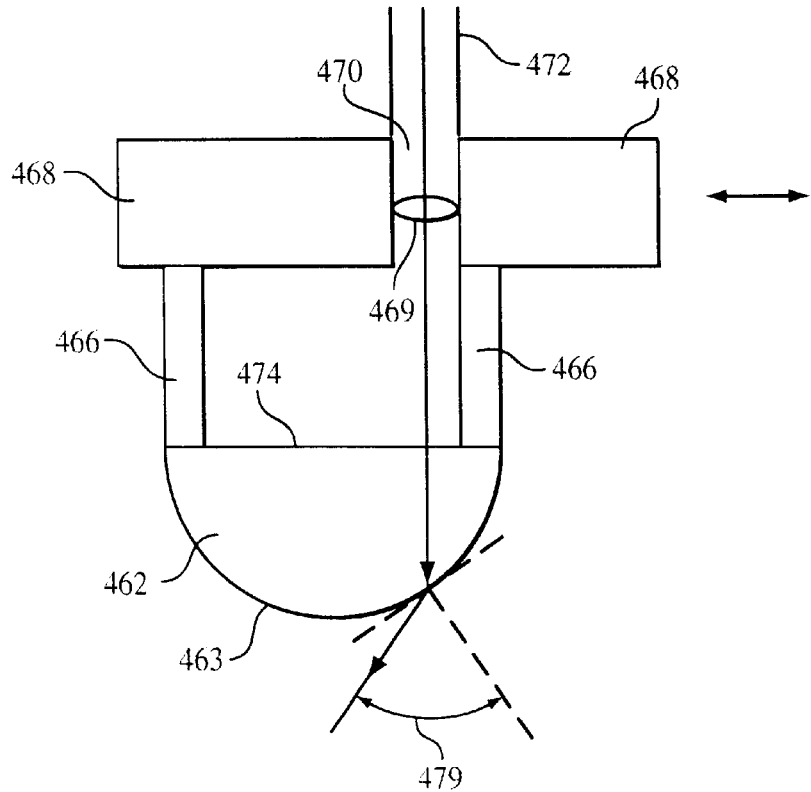

Referring to FIG. 4a, an optical coupler device 460 includes a shaped, e.g., hemispherical or hemicylindrical, optical coupler 462, a first support 466, and a second support 468. Optical coupler 462 has a contoured surface 463, which, in this embodiment, is also the tissue-contacting surface. Optical coupler 462 is mounted to the first support 466, which is slidably connected to the second support 468. The second support 468 includes an aperture 470 that is aligned with an optical fiber 472 coupled to the second support. Optical fiber 472 delivers laser energy through aperture 470 to contact the back face 474 of optical coupler 462 at substantially normal incidence. Second support 468 can also include a collimating lens 469 positioned to collimate the laser energy prior to it impinging on optical coupler 462.

The laser energy contacts the front face (contoured surface 463) of optical coupler 462 at an angle of incidence that depends on the relative position of the first and second supports 466 and 468. By translating the relative position of first support 466 and second support 468, as shown in FIG. 4b, the laser energy contacts a different part of contoured surface 463 at a correspondingly different angle of incidence. As shown in both FIGS. 4a and 4b, the different incident angles give rise to different refracted angles 479 and 479' and the correspondingly different penetration depths. Optical coupler device 460 can further include or incorporate any of the other features described previously.

The embodiments of FIGS. 3a, 3b, 4a, and 4b are examples of laser coupling devices in which a relative change in angular orientation or a relative translation between components of the optical coupler device is used to selectively vary the incident angle at which the laser energy contacts the tissue-contacting surface of the optical coupler. In another embodiment, such as that shown in FIG. 5, the optical coupler device can be monolithic, but is designed to include multiple tissue-contacting surfaces each corresponding to a different incident angle for the laser energy.

Figure 5:
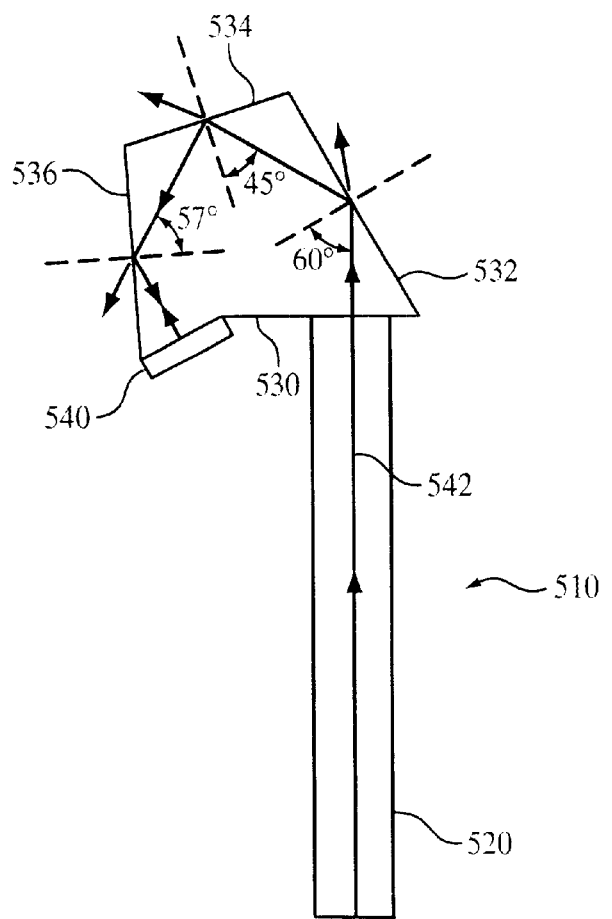
FIG. 5 is a schematic diagram of another embodiment of an optical coupler device.

Referring to FIG. 5, an optical coupler device 510 includes a support structure 520 and an optical coupler 530 connected to the support structure. In the presently described embodiment, optical coupler includes three tissue-contacting surfaces 532, 534, and 536, respectively. Other embodiments may include more or less than three such surfaces. Support structure 520 delivers laser energy 542 into optical coupler 530 and causes the laser energy to be incident on first tissue-contacting surface 532 at a first angle greater than that for total internal reflection for an air and/or water interface. Upon such reflection, the geometry of optical coupler 530 causes the laser energy to reflect from first surface 532 to second tissue-contacting surface 534 at a second angle greater than that for total internal reflection for an air and/or water interface. Similarly, upon such reflection, the geometry of optical coupler 530 causes the laser energy to reflect from second surface 534 to third tissue-contacting surface 536 at a third angle greater than that for total internal reflection for an air and/or water interface. The first, second, and third angles are different from one another, and in FIG. 5, for example, are shown to be 60°, 45°, and 57°, respectively.

During use, a surgeon manipulates optical coupler 530, either directly or indirectly, to contact tissue with a selected one of the first, second, and third surfaces 532, 534, and 536, respectively, to cause the laser energy to couple from optical coupler 530 into the tissue at an angle of incidence corresponding to a selected optical penetration depth. The other surfaces not contacting tissue totally internally reflect any laser incident on them. Optical coupler 530 can further include a reflective coating 540 to retroreflect light reflected from third surface 536 back through the optical coupler.

Alternatively, reflective coating can be replaced with a beam dump as described previously. Furthermore, a detector can be positioned at the beam dump to measure the reflectance and guide the incident angle position in either a manual or automated procedure. Optical coupler device 510 can further include or incorporate any of the other features described previously.

Figure 6A:
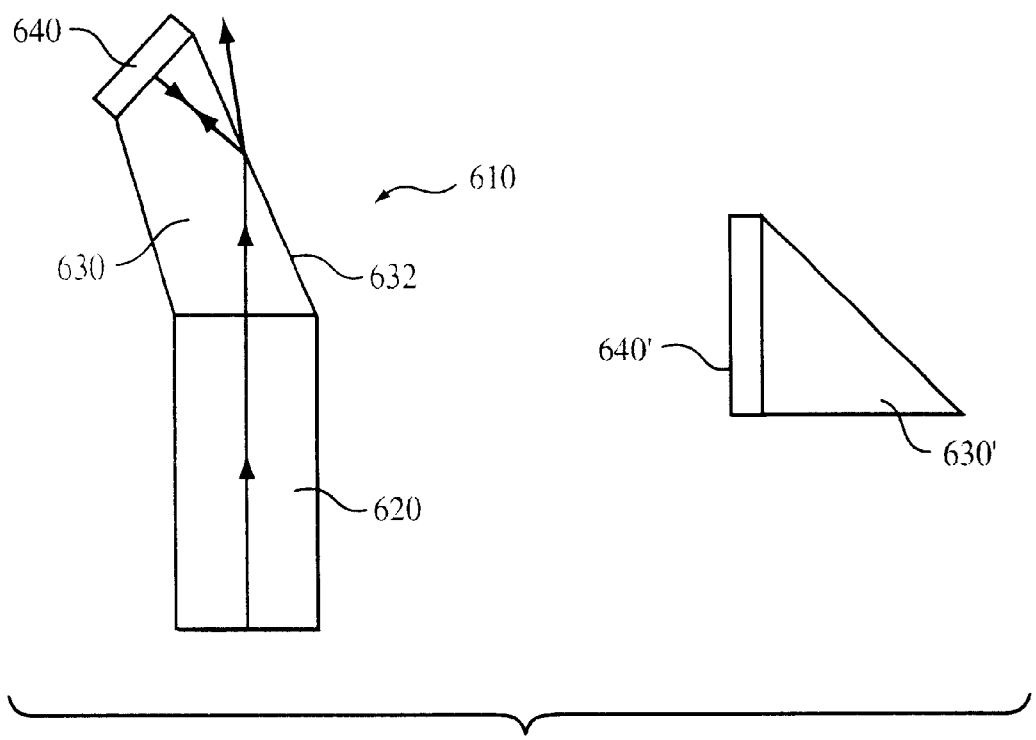
FIGS. 6a and 6b are schematic diagrams of another embodiment of an optical coupler device.
Figure 6B:
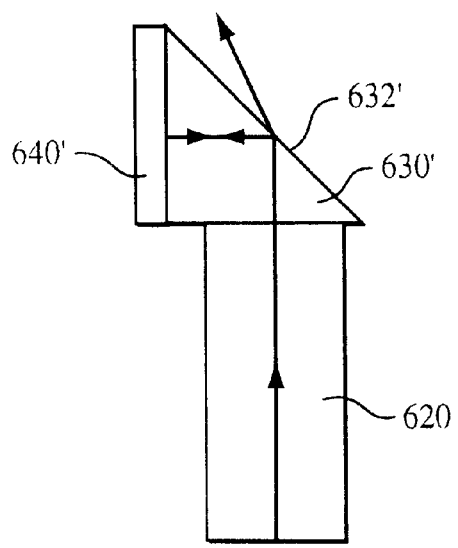

In another embodiment shown in FIG. 6a, an optical coupler device 610 can include an optical coupler base 620 and one of multiple optical coupler tips 630, 630', and 630" removably connected to the base 620. The removable connection between the optical coupler tip 630 and optical coupler base 620 can be, e.g, based on a friction fit, locking mechanism, clamp, or adhesive. Base 620 delivers laser energy into optical coupler 630 and causes the laser energy to be incident on a tissue-contacting surface 632 at an angle greater than that for total internal reflection for an air interface. For example, the angle shown in FIG. 6a is 60° for optical coupler tip 630. The geometry of each optical coupler tip differs to produce a different incident angle for the laser radiation. For example, FIG. 6b shows optical coupler tip 630' connected to base 620 to produce an incident angle of 45°. During use, a surgeon selects an optical coupler tip defining an incident angle corresponding to a desired optical penetration depth for the laser energy. As in the embodiment of FIG. 5, each optical coupler tip 630 can include a reflective coating 640 to retroreflect light reflected from the tissue-contacting surface 632 back through the optical coupler. Alternatively, reflective coating can be replaced with a beam dump as described previously. Optical coupler device 610 can further include or incorporate any of the other features described previously.

Suitable materials for any of the optical couplers described above include, e.g., sapphire, fused silica, BK-7 glass, flint glass, germanium, and zinc selenide. The choice of material depends in part on the wavelength of the laser energy being used and the refractive index and absorption coefficient of the tissue being contacted.

Suitable laser sources include, e.g., a Nd:YAG laser, CTE:YAG laser, ErCr:YSGG laser, holmium laser, erbium laser, $CO_2$ laser, diode laser, dye laser, and flash lamps. In preferred embodiments, pulsed laser systems are preferred for superficial alteration, e.g., ablation or photochemical alteration, of a substrate. Other lasers can be used as long as the proper wavelengths and pulse-widths are achieved as described above. Each laser described below has different advantages.

Pulsed $CO_2$ lasers, for example "superpulsed" $CO_2$ surgical lasers, or very powerful transverse excited atmospheric (TEA) $CO_2$ lasers having a 0.2 $\mu$s pulse-width and up to 2 J per pulse at 10.6 $\mu$m multiline output, e.g., those manufactured by Lumonics, London, England, are capable of generating ablation of tissue.

Normal-mode pulsed holmium lasers, e.g., a Model 123, manufactured by SEO, Inc., Concord, Mass., and short-pulsed holmium lasers (0.5 to 10 $\mu$s, 2 $\mu$m), e.g., a cryogenic holmium/thulium laser, manufactured by Rare Earth, Inc., Dennis, Mass., are useful for laser tissue ablation.

Flashlamp-pumped tunable dye lasers operating in the visible spectrum, e.g., those manufactured by Candela Laser Corporation, Wayland, Mass., in which the laser pulse duration can be varied between 0.3 and 10 $\mu$s at wavelengths where the absorption coefficient, $\mu_a$, can be varied from 10 to 1000 $cm^{-1}$, can also be used. This laser facilitates the choice of wavelength, the determination of pulse duration effects, and the control over the early events of cavitation-induced energy decoupling.

Each laser can be coupled via a collimated beam of 1 to 5 mm diameter with a spatial beam intensity distribution as close to flat as possible, to the optical coupler. The material for the optical coupler can be chosen to minimize absorption losses at the wavelength of the source, for example, germanium for a $CO_2$ source, fused silica and sapphire optical couplers for visible and near-infrared sources such as holmium and tunable dye lasers, and silicon for use with the holmium laser and others operating near the 2 μm wavelength.

Optimal parameters can be tested on biological tissue in vitro using routine procedures, e.g., by gradually increasing laser energy intensity coupled into the wave generator until ablation is visually observed. The tissue can then be analyzed, e.g., microscopically, to ensure that the desired penetration depth has been achieved. The penetration depth and energy intensity required for ablation can then be adjusted according to the equations described above.

Applications

The optical coupler devices can be used in a wide range of photomedical applications such as precise manipulation, resurfacing, and ablation of dermal and epidermal layers of skin and subcutaneous fat. Further applications follow below.

Skin Resurfacing

The optical coupler devices described above can be used for skin resurfacing in, for example, cosmetic procedures. Both superfical surface heating and/or ablation of skin, as well as subsurface heating and/or ablation of skin is possible. In either case, one of the optical couplers described herein delivers optical energy into the target tissue at the desired depth by controlling the incident angle of the optical radiation. To accomplish subsurface heating and/or ablation, cooling elements are used to cool the skin surface causing the optically induced thermal peak to reside at a subsurface depth. Thus, cooling is appropriate for non-ablative skin rejuvenation. For example, the epidermis is spaced from ablation or necrosis by cooling, while the dermis (which underlies the epidermis, beginning about 0.1 mm below the surface) is heated to at least 55° C. such that cellular injury occurs. This causes remodelling, or rejuvenation by replacement of old dermis. Such subsurface heating can be appropriate for cosmetic procedures because the tissue healing and scaring occurs below the skin surface. Nonetheless superficial surface heating and/or ablation may also be appropriate depending on the procedure.

One such cosmetic procedure is wrinkle smoothing. Wrinkles are formed from redundant skin. Wrinkle smoothing requires the superficial or subsuperficial ablation of the ridges of skin that cause wrinkles to appear. Most wrinkles are fine, e.g., less than 1 mm wide, but more noticeable wrinkles are typically larger than 1 mm wide. In addition to the use of the optical couplers described above for wrinkle smoothing, the invention includes another method for wrinkle smoothing that is particularly suitable for larger wrinkles and is not limited to optical couplers capable of providing a selectable incident angle for the optical energy being directed to the skin.

Figure 7:
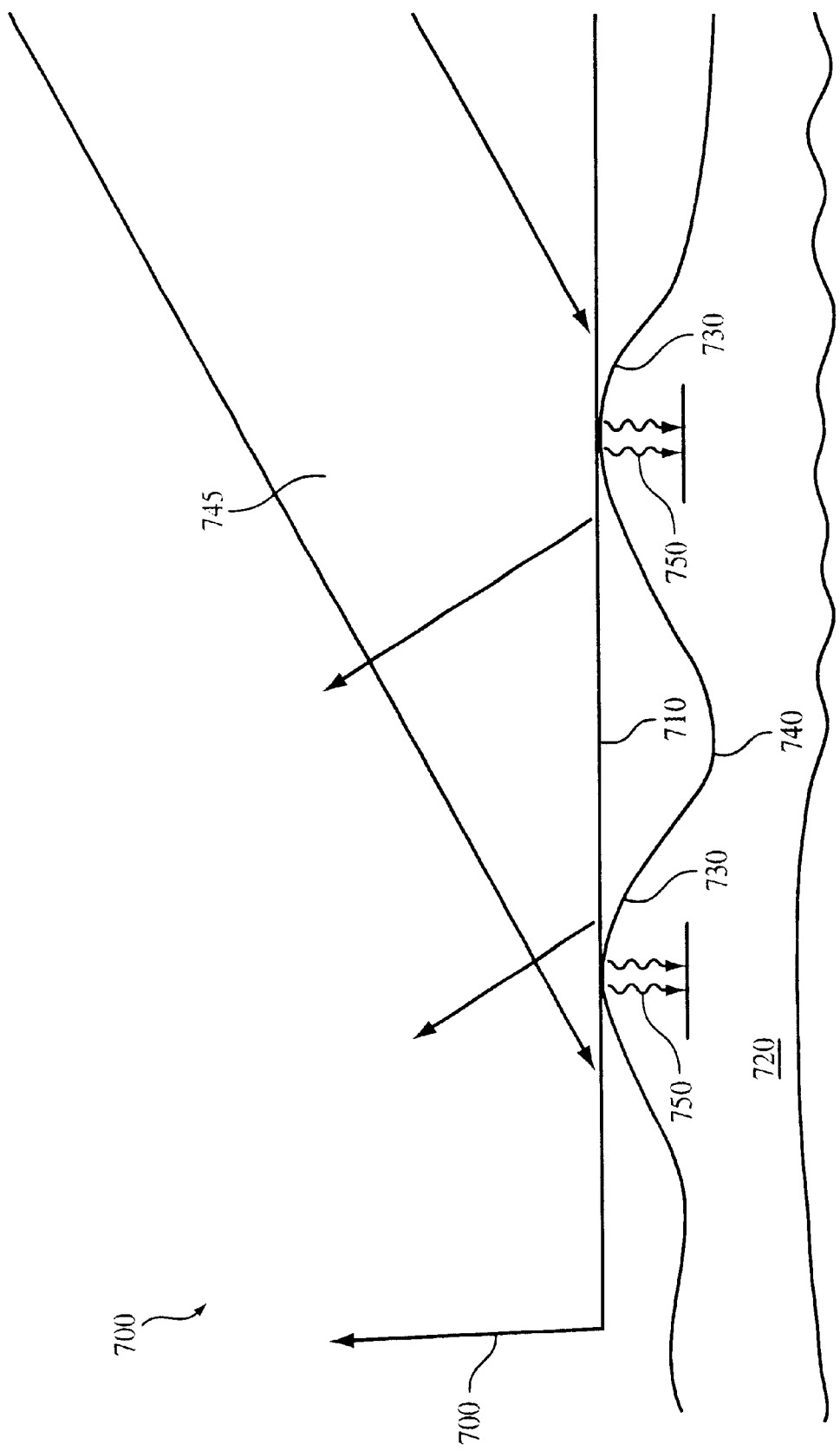
FIG. 7 is a schematic diagram of a method of smoothing wrinkles using the optical coupler devices described herein.

Referring to FIG. 7, a surgeon contacts the tissue-contacting surface 710 of an optical coupler 700 to a region of skin 720 containing a wrinkle. The surface profile of the wrinkle causes the tissue-contacting surface to contact the ridges 730 of the wrinkle, but not the valleys 740 of the wrinkle. Because the laser energy 745 is delivered to the tissue-contacting surface at an incident angle greater than that for total internal reflection for an air and/or water interface, refracted laser energy 750 is only coupled to the ridges of the wrinkle.

Optical Resonator Ablation Device for Laser Angioplasty and Other Endoluminal Ablation To date, laser recanalization is used mainly to assist access for balloon angioplasty, rather than to create a new round, smooth lumen. Even after a "drilling" laser angioplasty or mechanical angioplasty device is used to gain access, it is necessary to debulk the tissue and to leave a smooth, round surface without perforation of the vessel walls. Specifically, the ideal system would: (1) create a smooth, round lumen of a predetermined size; (2) produce minimal thermal injury to tissue; (3) produce debris smaller than about 7 μm, the size of red blood cells; (4) deliver light directly to the inner walls of vessels; and (5) avoid perforation.

According to the present invention, optical coupler devices delivering laser energy to controlled optical penetration depths can be used to create such a lumen, without excessive tissue injury, and with appropriately small debris size, using fiber-compatible laser wavelengths that when used as a free beam penetrate too deeply and damage otherwise healthy tissue.

Corneal Laser Ablation Devices

The optical coupler devices described herein can also be used for corneal refractive laser surgery. Refracted waves having a controlled optical penetration depth can be used to ablate a cornea to a precisely predetermined and conventional optically correct surface shape with minimal thermal injury using lasers that are simpler and more reliable than the 193 nm excimer laser systems typically used for corneal ablation.

Human Stratum Corneum Removal Device

The laser coupler devices described herein may also be used to removal human stratum corneum for drug delivery by controlling the optical penetration depth. According to one embodiment, a laser, such as a diode-pumped solid state holmium microchip laser, may be used. These lasers are small, portable, and can even be battery-powered, with high reliability and long life. Thus, the device makes it possible to apply a highly desirable, but otherwise inapplicable, laser for this application.

Endodontal Root Canal and Dental Laser Ablation Devices

Endodontal root canal and caries removal procedures require control over the laser interaction depth to limit thermal injury. The laser coupler devices described herein, which provide control over optical penetration depth, are suitable for these dental applications. The refracted wave propagation allows tooth-cutting laser pulses that are fiber optic-compatible.

Other embodiments are within the scope of the following claims.

What is claimed is:

1. An apparatus delivering laser radiation to a substrate at a controlled penetration depth, the substrate having a first refractive index and an absorption coefficient $\mu_a$, said apparatus comprising an optical coupler for receiving optical energy from a optical energy source, the optical coupler having a second refractive index higher than the first refractive index, the optical coupler being adapted to contact and form an interface with the substrate, the optical coupler having a contoured surface such that an angle of refraction $\theta_r$ of the optical energy into the substrate at the interface can be varied by adjusting relative positions of the optical coupler and the optical energy entering the optical coupler, selection of a particular angle of refraction producing a desired penetration depth $\delta_r$ according to the equation $\delta_r \approx (1/\mu_a)\cos\theta_r$, and a positioning mechanism coupling the optical coupler and the optical energy for adjusting the relative positions of the optical coupler and the optical energy entering the optical coupler.

2. The apparatus of claim 1, wherein the optical coupler has a hemispherical shape.

3. The apparatus of claim 1, wherein the optical coupler has a hemicylindrical shape.

4. The apparatus of claim 1, wherein the positioning mechanism is an angular positioning mechanism.

5. The apparatus of claim 4, wherein the angular positioning mechanism comprises a gimbal mounted to the optical coupler.

6. The apparatus of claim 1, wherein the positioning mechanism is a translational positioning mechanism.

7. The apparatus of claim 6, wherein the translational positioning mechanism comprising a support structure slidably connected to the optical coupler.

8. The apparatus of claim 1, further comprising an optical fiber for delivering the optical energy to the optical coupler.

9. The apparatus of claim 8, wherein the optical fiber is mechanically coupled to the positioning mechanism.

10. The apparatus of claim 1, wherein the optical coupler is made from one of sapphire, fused silica, BK-7 glass, flint glass, germanium, and zinc selenide.

11. The apparatus of claim 1, further comprising the optical energy source.

12. The apparatus of claim 11, wherein the optical energy source comprises a Nd:YAG laser, CTE:YAG laser, ErCr:YSGG laser, holmium laser, erbium laser, $CO_2$ laser, diode laser, dye laser, or a flash lamp.

13. The apparatus of claim 1, wherein the optical coupler is configured to receive the optical energy at substantially normal incidence and deliver the optical energy to the interface at non-normal incidence.

14. An apparatus delivering laser radiation to a substrate at a controlled penetration depth, the substrate having a first refractive index $n_1$ and an absorption coefficient $\mu_a$, said apparatus comprising an optical coupler for receiving optical energy from a optical energy source, the optical coupler having a second refractive index $n_2$ higher than the first refractive index, the optical coupler having at least two surfaces adapted to contact and form an interface with the substrate, wherein the optical coupler is shaped to internally direct the optical energy received from the optical energy source to the first surface at a first acute incident angle, and direct optical energy internally reflected from the first surface to the second surface at a second acute incident angle different from the first acute incident angle, wherein contacting the substrate with the first surface produces an optical penetration depth $\delta_{r1}(1/\mu_a)\cos\theta_{r1}$, and contacting the substrate with the second surface produces an optical penetration depth $\delta_{r2}(1/\mu_a)\cos\theta_{r2}$, where $\theta_{r1}$ is the refraction angle corresponding to the first acute incident angle and $\theta_{r2}$ is the refraction angle corresponding to the second acute incident angle.

15. The apparatus of claim 14, wherein the optical coupler has a third surface adapted to contact and form an interface with the substrate, and wherein the optical coupler is shaped to direct the optical energy internally reflected from the second surface to the third surface at a third acute incident angle.

16. The apparatus of claim 14, wherein the first and second acute incident angles are both greater than arcsin $(n_0 n_2)$, $n_0$ being the refractive index for air.

17. The apparatus of claim 14, where in the first and second acute incident angles are both less than $\arcsin(n_1/n_2)$.

18. The apparatus of claim 14, wherein the first and second acute incident angles are each greater than a bout 10°.

19. The apparatus of claim 14, further comprising an optical fiber mechanically coupled to the optical coupler to deliver the optical energy from the optical energy source into the optical coupler.

20. The apparatus of claim 14, wherein the optical coupler is made from one of sapphire, fused silica, BK-7 glass, flint glass, germanium, and zinc selenide.

21. The apparatus of claim 14 further comprising the optical energy source.

22. The apparatus of claim 21, wherein the optical energy source comprises a Nd:YAG laser, CTE:YAG laser, ErCr:YSGG laser, holmium laser, erbium laser, $CO_2$ laser, diode laser, dye laser, or a flash lamp.

23. An apparatus delivering laser radiation to a substrate at a controlled penetration depth, the substrate having a first refractive index $n_1$ and an absorption coefficient $\mu_a$, said apparatus comprising an optical coupler base; and a plurality of optical coupler tips each configured to be mechanically attached to the optical coupler base to form an optical coupler for delivering optical energy from a optical energy source to a substrate, the optical coupler comprising a surface adapted to contact and form an interface with the substrate, wherein each optical coupler tip, when attached to the optical coupler base, is shaped to internally deliver the optical energy to the interface at an incident angle, wherein the incident angles corresponding to each of the plurality of optical coupler tips differ from one another, whereby selecting one of the optical coupler tips specifies a desired penetration depth $\delta_r$ according to the equation $\delta_r \approx (1/\mu_a)\cos\theta_r$, where $\theta_r$ is the refraction angle corresponding to the incident angle defined by the selected optical coupler tip.

24. The apparatus of claim 23, wherein each of the optical coupler tips has a refractive index greater than the first refractive index $n_1$.

25. The apparatus of claim 23, wherein the plurality of optical coupler tips comprises at least three optical coupler tips.

26. The apparatus of claim 23, wherein the incident angle defined by each optical coupler tip is greater than about 10°.

27. The apparatus of claim 23, wherein the incident angle defined by each optical coupler tip is greater than $\arcsin(n_0/n_2)$, where $n_0$ is the refractive index for air and $n_2$ is the refractive index of the respective optical coupler tip.

28. The apparatus of claim 23, wherein the incident angle defined by each optical coupler tip is less than $\arcsin(n_1/n_2)$, where $n_2$ is the refractive index of the respective optical coupler tip.

29. The apparatus of claim 23, further comprising an optical fiber mechanically coupled to the optical coupler base.

30. The apparatus of claim 23, wherein each optical coupler tip is made from one of sapphire, fused silica, BK-7 glass, flint glass, germanium, and zinc selenide.

31. The apparatus of claim 23 further comprising the optical energy source.

32. The apparatus of claim 31, wherein the optical energy source comprises a Nd:YAG laser, CTE:YAG laser, ErCr:YSGG laser, holmium laser, erbium laser, $CO_2$ laser, diode laser, or dye laser.

33. A method of removing wrinkles in a region of skin, the method comprising:

applying an optical coupler to the region to cause a surface of the optical coupler to contact the ridges of the wrinkles and be spaced from the valleys of the wrinkles; and delivering optical energy from a optical energy source through the optical coupler to the surface at an incident angle that is greater than about $\arcsin(n_0/n_2)$ and less than about $\arcsin(n_1/n_2)$, where $n_0$, $n_1$, and $n_2$ are the refractive indices of air, the skin, and the optical coupler, respectively, wherein the optical energy is delivered with energy sufficient to smooth over the ridges of the wrinkles.

34. The method of claim 33, wherein the optical energy is delivered to the optical coupler though an optical fiber.

35. The method of claim 33, wherein the optical coupler is made from one of sapphire, fused silica, BK-7 glass, flint glass, germanium, and zinc selenide.

36. The method of claim 33, wherein the optical energy source comprises a Nd:YAG laser, CTE:YAG laser, ErCr:YSGG laser, holmium laser, erbium laser, $CO_2$ laser, diode laser, or dye laser.

* * * * *

UNITED STATES PATENT AND TRADEMARK OFFICE
CERTIFICATE OF CORRECTION

PATENT NO.   : 6,529,543 B1
DATED        : March 4, 2003
INVENTOR(S)  : R. Rox Anderson, M.D., Ph.D. and Dr. Yacov Domankevitz It is certified that error appears in the above-identified patent and that said Letters Patent is hereby corrected as shown below:

Title page,
Item [56], References Cited, U.S. PATENT DOCUMENTS, replace "10/1978" with -- 10/1998 --

Column 1,
Line 67, replace "a" with -- an --

Column 2,
Lines 29 and 62, replace "a" with -- an --

Column 3,
Line 4, before "according" delete ","
Line 27, replace "including" with -- include --
Line 28, replace "includes" with -- include --
Line 39, replace "a" with -- an --

Column 5,
Line 14, replace "a" with -- $\alpha$ --

Column 7,
Line 20, replace "$\theta_i$" with -- $\theta_c$ --

Column 14,
Line 66, replace "a" with -- an --

Column 15,
Line 52, replace "a" with -- an --

UNITED STATES PATENT AND TRADEMARK OFFICE
CERTIFICATE OF CORRECTION

PATENT NO.      : 6,529,543 B1
DATED           : March 4, 2003
INVENTOR(S)     : R. Rox Anderson, M.D., Ph.D. and Dr. Yacov Domankevitz It is certified that error appears in the above-identified patent and that said Letters Patent is hereby corrected as shown below:

<u>Column 16,</u>
Line 14, replace "where in" with -- wherein --
Line 16, replace "a bout" with -- about --
Line 39, replace "a" with -- an --

<u>Column 18,</u>
Line 1, replace "a" with -- an --

Signed and Sealed this

Sixteenth Day of September, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,529,543 B1  Page 1 of 1
APPLICATION NO. : 09/717779
DATED : March 4, 2003
INVENTOR(S) : R. Rox Anderson and Yacov Domankevitz It is certified that error appears in the above-identified patent and that said Letters Patent is hereby corrected as shown below:

Title Page, Item [56] References Cited U.S. Patent Documents, replace "10/1978" with --10/1998--
Col. 1, line 67, replace "a" with --an--
Col. 2, line 29, replace "a" with --an--
Col. 2, line 62, replace "a" with --an--
Col. 3, line 4, before "according" delete ","
Col. 3, line 27, replace "including" with --include--
Col. 3, line 28, replace "includes" with --include--
Col. 3, line 39, replace "a" with --an--
Col. 5, line 14, replace "a" with --α--
Col. 7, line 20, replace "$\theta_i$" with --$\theta_c$--
Col. 14, line 66, replace "a" with --an--
Col. 15, line 52, replace "a" with --an--
Col. 16, line 14, replace "where in" with --wherein--
Col. 16, line 16, replace "a bout" with --about--
Col. 16, line 39, replace "a" with --an--
Col. 18, line 1, replace "a" with --an--

Signed and Sealed this

Fourteenth Day of December, 2010

David J. Kappos
*Director of the United States Patent and Trademark Office*